(12) United States Patent
Weese et al.

(10) Patent No.: US 9,953,040 B2
(45) Date of Patent: Apr. 24, 2018

(54) ACCESSING MEDICAL IMAGE DATABASES USING MEDICALLY RELEVANT TERMS

(75) Inventors: Juergen Weese, Aachen (DE); Helko Lehmann, Aachen (DE); Yuechen Qian, Eindhoven (NL); Warner Rudolph Theophile Ten Kate, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 570 days.

(21) Appl. No.: 12/671,256

(22) PCT Filed: Jul. 25, 2008

(86) PCT No.: PCT/IB2008/052983
§ 371 (c)(1),
(2), (4) Date: May 20, 2010

(87) PCT Pub. No.: WO2009/016559
PCT Pub. Date: Feb. 5, 2009

(65) Prior Publication Data
US 2010/0293164 A1    Nov. 18, 2010

(30) Foreign Application Priority Data
Aug. 1, 2007   (CN) .......................... 2007 1 0138409

(51) Int. Cl.
G06F 17/30    (2006.01)
G06F 19/00    (2018.01)
(52) U.S. Cl.
CPC .. G06F 17/30265 (2013.01); G06F 17/30268 (2013.01); G06F 19/321 (2013.01)
(58) Field of Classification Search
CPC ......... G06F 17/30265; G06F 17/30268; G06F 19/321
See application file for complete search history.

(56) References Cited

U.S. PATENT DOCUMENTS 5,128,865 A * 7/1992 Sadler .................. G06F 17/271
704/2
2003/0013951 A1* 1/2003 Stefanescu et al. .......... 600/407
(Continued)

FOREIGN PATENT DOCUMENTS

WO    WO 2005/048193    *   5/2005
WO       2007056601 A2      5/2007

OTHER PUBLICATIONS

Aurdal, L.; Model based segmentation; Course Notes Online; Nov. 13, 2008 http://www.aurdalweb.com/modbased_articles.pdf.
Bontas, E. P., et al.; Generation and Management of a Medical Ontology in a Semantic Web Retrieval System; 2004; Lecture Notes in Computer Science; vol. 3290; pp. 637-653.
Das, S., et al.; Supporting Ontology-based Semantic Matching in RDBMS; 2004; Proc. Int'l. Conf. on Very Large Databases; pp. 1054-1065.
(Continued)

*Primary Examiner* — Alicia Willoughby (57) ABSTRACT

A system for accessing a database of a plurality of image data sets includes an acquisition unit which acquires a query for searching the database for an image data set or an image data subset comprised in an image data set. The query includes at least one medically relevant term which defines a search criteria. A determining unit determines the image data set or the image data subset included in the image data set based on the strength of semantic matches between the at least one medically relevant term and (a) corresponding medical annotation(s) describing the image data set. A retrieving unit retrieves the determined image data set or image data subset from the database.

8 Claims, 5 Drawing Sheets

(56) References Cited

U.S. PATENT DOCUMENTS

| | | | |
|---|---|---|---|
| 2003/0069503 A1* | 4/2003 | Matsui | 600/437 |
| 2003/0194057 A1* | 10/2003 | Dewaele | G06T 7/0012 378/210 |
| 2005/0070783 A1* | 3/2005 | Yanagita | A61B 6/00 600/407 |
| 2005/0234355 A1* | 10/2005 | Rowlandson | A61B 5/02405 600/509 |
| 2006/0036592 A1* | 2/2006 | Das et al. | 707/4 |
| 2006/0041564 A1* | 2/2006 | Jain et al. | 707/100 |
| 2006/0078194 A1 | 4/2006 | Fradkin et al. | |
| 2006/0165268 A1 | 7/2006 | Kaus et al. | |
| 2008/0027917 A1* | 1/2008 | Mukherjee et al. | 707/3 |
| 2008/0037852 A1* | 2/2008 | Zhou et al. | 382/132 |
| 2008/0140706 A1* | 6/2008 | Kahn | 707/103 R |
| 2008/0247618 A1* | 10/2008 | Laine | G06F 19/321 382/128 |
| 2010/0119134 A1* | 5/2010 | Dewaele | 382/128 |
| 2010/0293164 A1 | 11/2010 | Weese et al. | |

OTHER PUBLICATIONS

Hu, B., et al.; Ontology-based Medical Image Annotation with Description Logics; 2003; IEEE 15th conf. on Tools with Artificial Intelligence; pp. 77-82.

Hyvonen, E., et al.; Ontogator: Combining View-and Ontology-Based Search with Semantic Browsing; 2003; Proc. of XML-Finland; http://www.cs.helsinki.fi/u/eahyvone/publications/xmlfinland2003/yomXMLFinland2003.pdf.

Schreiber, A. T., et al.; Ontology-based photo annotation; 2001; IEEE Intelligent Systems; 16(3)66-74.

Koninklijke Philips Electronics N.V.; "Accessing Medical Image Databases Using Anatomical Shape Information"; patent application No. 06300994.8 filed Sep. 29, 2006.

Ya-Jun, L. et al., "Integrated semantic similarity model based on ontology". Wuhan University Journal of Natural Sciences, Sep. 1, 2004, CN, vol. 9, Nr: 5, pp. 601-605.

\* cited by examiner

ACCESSING MEDICAL IMAGE DATABASES USING MEDICALLY RELEVANT TERMS

FIELD OF THE INVENTION

The invention relates to the field of accessing a database comprising a plurality of image data sets, and more particularly to a system and method for accessing a medical image database comprising a plurality of image data sets, using medically relevant terms. Furthermore, the invention relates to a computer program for implementing said method on a computer.

BACKGROUND OF THE INVENTION

As medical imaging technologies advance, more and more 3D image data sets are acquired by medical scanners and stored in image databases, such as Picture Archiving and Communication Systems (PACS). Such systems contain a huge amount of medical cases that could be of value to radiologists for improving clinical decisions and treatment plans based on this available data.

European patent application entitled "Accessing Medical Image Databases Using Anatomical Shape Information", filed by Koninklijke Philips Electronics N.V on Sep. 29, 2006 under application number 06300994.8 (not disclosed yet), describes a system for retrieving a volumetric data subset comprised in a data storage for volumetric image sets, the system comprising a first query unit for composing a first query for retrieving the data storage for a volumetric image data set comprising the volumetric image data subset; a second query unit for composing a second query for retrieving the volumetric image data set for the volumetric image data subset, the second query comprising anatomical structure information for identifying an anatomical structure within the volumetric image data set; a first determination unit for determining the volumetric image data set, based on the first query; a second determination unit for determining the volumetric image data subset of the volumetric image data set, based on the anatomical structure identified within the volumetric image data set, using the anatomical structure information comprised in the second query; and a retrieval unit for retrieving the determined volumetric image data subset. The system is thus capable of retrieving a reduced amount of data describing the anatomical structure, i.e., a subset of a volumetric image data set, based on anatomical shape information.

SUMMARY OF THE INVENTION

Amongst others it is an object of the invention to provide a system for retrieving an image database, using medically relevant terms that are meaningful for medical diagnosis and treatments.

To this end this invention provides a system for accessing a database comprising a plurality of image data sets, the system comprising:

an acquiring unit for acquiring a query for searching the database for an image data set or an image data subset comprised in an image data set, the query comprising at least one medically relevant term defining search criteria;

a determining unit for determining the image data set or the image data subset comprised in the image data set, based on the strength of semantic matches between the at least one medically relevant term and (a) corresponding medical annotation(s) describing the image data set; and a retrieving unit for retrieving the determined image data set or image data subset from the database.

By enabling semantic matches between medical annotations describing an image data set and the medically relevant term comprised in the query, this invention makes it possible to search for medical images with high-level medical information that is meaningful for medical diagnosis and treatments.

In an embodiment of the system, the medically relevant term comprises any one of an anatomically and diagnostically relevant term, and the medical annotation comprises any one of an anatomical and a diagnostic annotation.

In another embodiment, the system comprises a segmenting unit for segmenting an image data set in the database into a plurality of image data subsets by adapting annotated shape models, using model-based segmentation, and generating for each of the image data subsets anatomical identifiers and associated annotations describing the image data set using corresponding annotated shape models for adaptation.

By transferring anatomical identifiers and associated annotations from annotated shape models for adaptation to the image data subsets, the system can automatically generate anatomical annotations for corresponding image data subsets that provide the basis for searching for the image data set/subset, using anatomically and diagnostically relevant terms.

It is another object of this invention to provide a method of retrieving an image database, using medically relevant terms that are meaningful for medical diagnosis and treatments.

To this end, the invention provides a method of accessing a database comprising a plurality of image data sets, the method comprising the steps of:

acquiring a query for searching the database for an image data set or an image data subset comprised in an image data set, the query comprising at least one medically relevant term defining search criteria;

determining the image data set or the image data subset comprised in the image data set, based on the strength of semantic matches between the at least one medically relevant term and (a) corresponding medical annotation(s) describing the image data set; and retrieving the determined image data set or image data subset from the database.

By enabling semantic matches between medical annotations describing an image data set and the medically relevant term comprised in the query, this invention makes it possible to search for medical images with high-level medical information that is meaningful for medical diagnosis and treatments.

In an embodiment of the method, the medically relevant term comprises any one of an anatomically and diagnostically relevant term, and the medical annotation comprises any one of an anatomical and a diagnostic annotation. The anatomically or diagnostically relevant term can be generated and stored in an electronic file stored in the database. Alternatively, the anatomically or diagnostically relevant term can be generated during the search and subsequently added to the electronic file for common queries.

In a further embodiment, the method further comprises steps for segmenting an image data set in the database into a plurality of image data subsets by adapting annotated shape models, using model-based segmentation, and generating for each of the image data subsets anatomical identifiers and associated annotations describing the image data set, using corresponding annotated shape models for adaptation.

By transferring anatomical identifiers and associated annotations from annotated shape models for adaptation to the image data subsets, the system can automatically generate anatomical annotations for corresponding image data subsets that provide the basis for searching for the image data set, using anatomically and diagnostically relevant terms.

It is a further object of the invention to provide a computer product that allows searching an image database using medically relevant terms that are meaningful for medical diagnosis and treatments. This is achieved by the invention by providing a computer program product to be loaded by a computer arrangement, comprising instructions for accessing a database comprising a plurality of image data sets, the computer arrangement comprising a processing unit and a memory, the computer program product, after being loaded, providing said processing unit with the capability to carry out the following tasks:

acquiring a query for searching the database for an image data set or an image data subset comprised in an image data set, the query comprising at least one medically relevant term defining search criteria;

determining the image data set or the image data subset comprised in the image data set, based on the strength of semantic matches between the at least one medically relevant term and (a) corresponding medical annotation(s) describing the image data set; and retrieving the determined image data set or image data subset from the database.

Modifications and variations thereof, of the inventions defined in independent claims, which correspond to modifications of the search system and variations thereof, being described, can be carried out by a skilled person on basis of the present description.

The skilled person will appreciate that the system may be applied to different image databases comprising two-dimensional (2D), three-dimensional (3D) and four-dimensional (4D) image data acquired by various acquisition modalities such as, but not limited to, Computed Tomography (CT), Magnetic Resonance Imaging (MRI), Ultrasound (US), Positron Emission Tomography (PET), Single Photon Emission Computed Tomography (SPECT), and Nuclear Medicine (NM).

DESCRIPTION OF THE DRAWINGS

The above and other objects and features of the present invention will become more apparent from the following detailed description considered in connection with the accompanying drawings, in which.

The same reference numerals are used to denote similar parts throughout the Figures.

DETAILED DESCRIPTION

Figure 1:
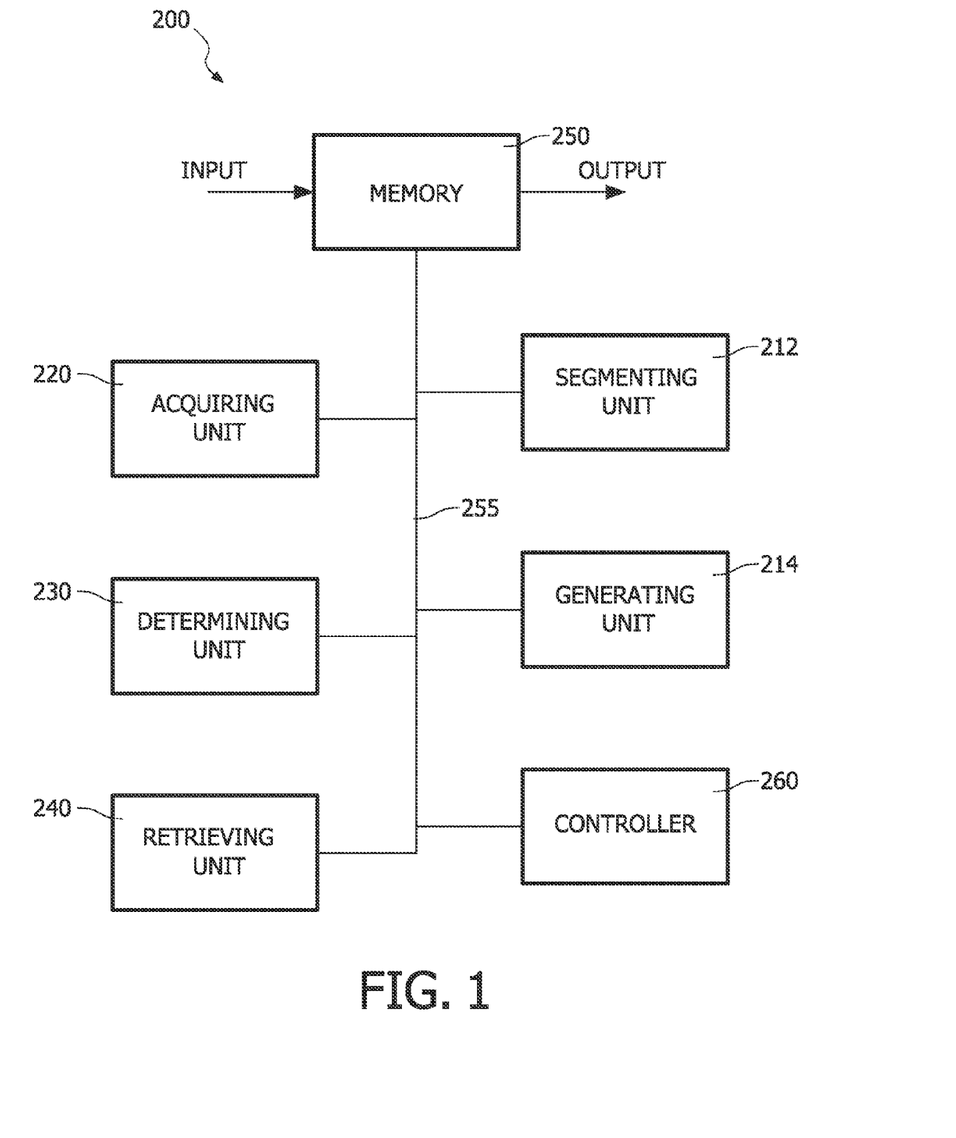
FIG. 1 is a block diagram showing an exemplary embodiment of a search system in accordance with the invention.

FIG. 1 is a block diagram showing an exemplary embodiment of a system 200 for accessing a database comprising a plurality of image data sets, the system comprising:

an acquiring unit 220 for acquiring a query for searching the database for an image data set or an image data subset comprised in an image data set, the query comprising at least one medically relevant term defining search criteria;

a determining unit 230 for determining the image data set or the image data subset, based on the strength of semantic matches between the at least one medically relevant term and (a) corresponding medical annotation(s) describing the image data set; and a retrieving unit 240 for retrieving the determined image data set or image data subset from the database.

The acquiring unit 220 is arranged to acquire a query from a user, for instance, from a radiologist or a resident doctor. The query comprises at least one medically relevant term that defines the search criteria for a wanted medical image data subset.

The determining unit 230 is arranged to search the database according to the search criteria to find the image data set or image data subset. The determination is based on the strength of semantic matches between the medically relevant term(s) comprised in the query and corresponding medical annotations describing the image data set. Here, the medically relevant term can be an anatomically and/or diagnostically relevant term, and the medical annotations can be anatomical and/or diagnostic annotations.

The strength of the semantic matches is derived by an examination, e.g. a reasoning process, of a medical ontology. The used medical ontologies are medical background knowledge banks describing different aspects related to medical cases, for example, the human anatomy, the disease and its etiology, the medical treatments, etc. These ontologies are maintained and made available on the Internet, for example. Examples of medical ontologies include the UMLS (Unified Medical Language System) and FMA (Foundational Model of Anatomy). The details of the determining unit 230 are described later in combination with an exemplary execution of a search.

The retrieving unit 240 is arranged to retrieve from the database the image data set or image data subset determined by the determining unit 230. The retrieved image data set or image data subset may be directed to an output device, for instance, a screen to display the medical image represented by the image data subset.

In an embodiment, the system 200 further comprises a segmenting unit for segmenting an image data set in the database into a plurality of image data subsets by adapting annotated shape models, using model-based segmentation, and generating for each of the image data subsets anatomical identifiers and associated annotations describing the image data set, using corresponding annotated shape models for adaptation.

When an image data set must be annotated, the mesh, i.e. the shape model, is adapted to the actual data by a model-based segmentation algorithm. After the adaptation, the shape model may be deformed to fit the actual data. However, while the direction of edges and the position of vertices may have been modified by the adaptation process, their anatomical identifiers remain unaltered. Hence each annotation of a subset of vertices and edges of the original shape model can be transferred to the corresponding vertices and edges of the adapted shape model, thereby generating an annotation of surfaces or voxel sets in the data set. The transferred anatomical identifiers and associated annotations form the original part of an electronic file describing the image data set.

In another embodiment, the system 200 further comprises a generating unit 214 for generating an anatomical annotation for the image data set, based on measures of anatomical structures in the regions identified by corresponding anatomical identifier(s) of image data subset(s) of the image data set and computation of two measures thereof. The generated anatomical annotation is associated with at least one anatomical identifier defining an image data subset of the image data set.

In another embodiment, the generating unit 214 is further arranged for generating a diagnostic annotation for the image data set, based on comparison of an anatomical annotation or a computing result of two anatomical annotations of the image data set and predefined criteria for use in a medical diagnosis. As any one of the anatomical annotations describing the image data set is associated with at least one anatomical identifier defining an image data subset of the image data set, the generated diagnostic annotation is associated with at least one image data subset.

The anatomical and diagnostic annotations generated by the generating unit 214 can be added to the electronic file as extension of the original annotations describing the image data set.

Optionally, the exemplary system 200 may also comprise the following units:

a memory unit 250 for storing image data sets, corresponding electronic files describing the image data sets and interim data of the system 200;

a controller 260 for controlling the workflow in the system 200; and a memory bus 255 for connecting all elements in the system 200.

Figure 2:
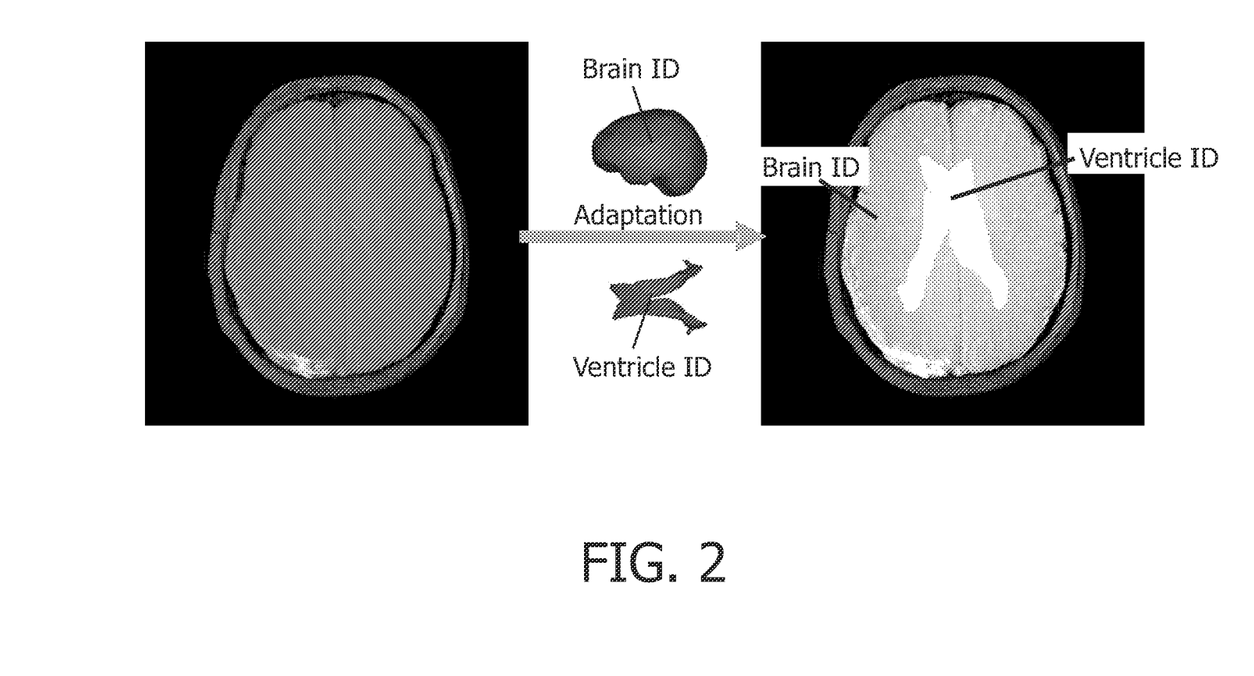
FIG. 2 schematically shows the generation of anatomical annotations in the segmentation unit of the system according to the invention.

FIG. 2 schematically shows the generation of anatomical annotations in the segmentation unit 212 of the system according to the invention.

The left part in FIG. 2 is a MRI (Magnetic Resonance Imaging) head image represented by an image data set. The shape models used for adaptation describe the brain surface and the ventricle, respectively. For simplicity, the complete brain surface is annotated with a single identifier "Brain ID". However subsets of the vertices/edges of the model could be annotated too, e.g. the vertices/edges belonging to the frontal lobe could be annotated with "Frontal Lobe ID". Similarly, all vertices/edges of the ventricle model are annotated with "Ventricle ID" for simplicity. By adaptation using model-based segmentation executed by the segmentation unit 212, the mesh model of the brain surface is mapped to the brain surface in the unknown imaging data set. Then voxels that are located at edges/vertices of the adapted model inherit all the associated annotations.

Furthermore, using additional knowledge associated with an identifier may enable annotation of other voxels. For example, the brain surface model can be used also to annotate all tissue enclosed within the surface. In this case, the identifier associated with the respective vertex/edge annotations is transferred to all voxels enclosed by the adapted mesh.

After an image data subset has been annotated in the above fashion, an electronic file is automatically generated that contains anatomical identifiers and associated annotations describing the anatomical features of the image data subset. The anatomical identifier and associated annotations form the original part of the electronic file.

The electronic file can be further enriched in many ways. In the above example, once the anatomical region is identified by the brain ID, the volumes or other measures of tissue, organs and lesions in the region can be generated and added to the set of annotations associated with the brain ID in the electronic file by the generating unit 214.

Furthermore, once the anatomical regions of the brain surface and the ventricle are identified by Brain ID and Ventricle ID, it is possible to calculate the ventricle-brain ratio for an image data set.

Assuming the set of annotations associated with "Brain ID" and "Ventricle ID" respectively comprise a number of voxels A identified as brain (the voxels are enclosed by the mesh part annotated as "Brain ID") and a number of voxels B identified as ventricle (the voxels are enclosed by the mesh part annotated as "Ventricle ID"), the ventricle-brain ratio can be approximated as B/A that can be automatically added to the set of annotations associated with "Brain ID" and/or "Ventricle ID".

Besides anatomically meaningful annotations, diagnostically meaningful annotations may also be generated and added to the electronic file. In the above example, the computed ventricle-brain ratio can be compared to a predefined value for use in a medical diagnosis. The process will be explained below.

Assuming the ventricle-brain ratio of a human being is very relevant to a disease like schizophrenia, determining whether or not the ventricle-brain ratio fits in the range of X±Y % may result in a diagnostically meaningful conclusion that can also be added to the electronic file as a diagnostic annotation.

The generating unit 214 may also be arranged to process the anatomical regions, using external CAD algorithms, thereby producing other medical information about the status of a disease. The anatomical information can be compared with information stored in encyclopaedias and other associated diagnostic information. Furthermore, other patient data, e.g. from the electronic patient record, can be incorporated into the electronic file. This provides a possibility for the system to search image data sets in databases with not only anatomically relevant terms but also diagnostically relevant terms.

The person skilled in the art will appreciate that the new annotations could be generated during the search process and added to a corresponding image report automatically. The new annotation, for example the ventricle-brain ratio, can also be pre-computed and added to the electronic file for common queries.

Figure 3:
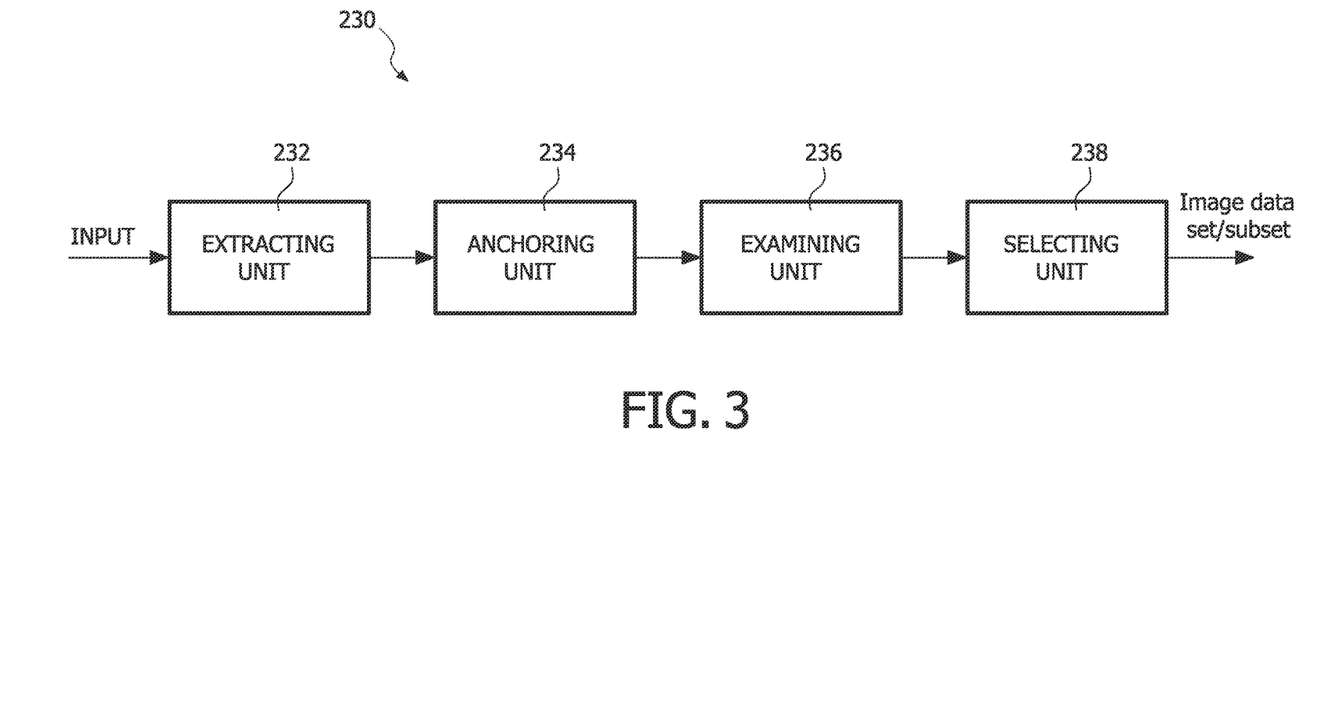
FIG. 3 is a block diagram showing an exemplary determining unit of the search system in accordance with the invention.

FIG. 3 is a block diagram showing an exemplary determining unit 230 of the retrieval system 200 in accordance with the invention. The determining unit 230 comprises an extracting unit 232, an anchoring unit 234, an examining unit 236 and a selecting unit 238.

The extracting unit 232 is arranged to extract keywords, e.g. the medically relevant term(s), from the query and the medical annotations from the electronic file describing the image data set in the database or the medical annotations generated during execution of a search. The medically relevant term comprises an anatomical and/or diagnostic term and the medical annotation comprises an anatomical and/or diagnostic annotation. The anchoring unit 234 is arranged to anchor the extracted keywords to the concepts in a medical ontology. The examining unit 236 is arranged to examine the relation between the so-anchored keywords from the query and those from the electronic files, based on the relationship between the concepts in the medical ontologies. The selecting unit 238 is arranged to select from the relations found by the examining unit those that are (the most) semantically related or, by selecting image data subsets from the image data sets in the database, those that are (the most) semantically related to the posed query.

The person skilled in the art will appreciate that the medical annotations extracted by the extracting unit 232 could be generated on the fly during the execution of searches. The medical annotations generated during searches may be added to the electronic file describing the corresponding image data set.

The work mechanism of the determining unit 230 can be explained in combination with a search example. Assuming each of the image data sets in the database is described by an electronic file, some electronic files comprise descriptions like "volume loss in hippocampus" and "brain tissue loss in temporal lobes". A query described as "find the brain image of male patients aged 65 who have brain tissue atrophy" is acquired by the acquiring unit 220 and passed to the determining unit 230.

First, to find a right medical image, e.g. a desired image subset, an anatomical term, such as "brain" in the query is identified and extracted by the extracting unit 232 in the determining unit 230. The extracted anatomical term "brain" is anchored into a first medical ontology, for example FMA, by the anchoring unit 234. The anchoring can be based on simple lexical similarity measures between the extracted keywords and the concept labels present in the background knowledge. In this example, a term called "brain" can be found in FMA.

Next, the extracting unit 232 is further arranged to identify anatomical annotations in the electronic file describing the image data set for determination. In the description of the electronic file, it finds the anatomical annotations "hippocampus" and "temporal lobes" The two anatomical annotations are anchored into the medical ontology, e.g., FMA, by the anchoring unit 234.

Then, the examining unit 236 is arranged to examine the relation between "brain" and "temporal lobes" as well as the relation between "brain" and "hippocampus", respectively. The strength of semantic matches between the anatomical term, e.g. "brain", comprised in the query and anatomical annotations, e.g. "hippocampus" or "temporal lobes" comprised in the electronic file is derived by a reasoning process, e.g., regarding the structure of anatomical relations set forth in the medical ontology, e.g., FMA.

In this example, for "brain" and "temporal lobes", the examining unit 236 finds that there is a part of a path between "temporal lobe" and "brain", namely if temporal lobe is a part of cerebral hemisphere, cerebral hemisphere is a part of telencephalon, telencephalon is a part of forebrain, and forebrain is a part of brain, hence temporal lobe is a part of brain. In this manner, the examining unit 236 knows "brain" and "temporal lobe" are semantically related. And meanwhile the image data subset described by "temporal lobe" can be identified.

A similar reasoning processing holds for "brain" and "hippocampus". Correspondingly, image data subsets described by the anatomical annotation "hippocampus" are identified.

Similarly, diagnostic terms, such as "atrophy" in the query, can be extracted from the query by the extracting unit 232 and further anchored into a second medical ontology, for example the UMLS. And meanwhile, the extracting unit 232 is further arranged to identify diagnostic annotations in the electronic file describing the image data set. The keywords "volume loss" and "tissue loss" are found and extracted from the electronic file. The extracted keywords "volume loss" and "tissue loss" are anchored into the medical ontology, e.g., UMLS, by the anchoring unit 234.

Subsequently, the examining unit 236 examines the relation between "atrophy" and "tissue loss". With the help of UMLS, the examining unit 236 finds that the diagnostic term "atrophy" in the query and the diagnostic annotation "tissue loss" describing the image data set are semantically related based on the similarity in meaning Correspondingly, the image data sets described by diagnostic annotations such as "tissue loss" and/or "volume loss" can be identified.

As described above, the generation of a diagnostic annotation for an image data set is based on comparison of an anatomical annotation or a computing result of two anatomical annotations of the image data set and predefined criteria for use in a medical diagnosis. As any one of the anatomical annotations is associated with at least one anatomical identifier defining an image data subset of the image set, the diagnostic annotation is thus associated with an image data subset that helps identify the desired image data subset.

Once the image subsets in the image data sets described by the anatomical or diagnostic annotations that are semantically related to the anatomical or diagnostic term defined in the query are identified, the selecting unit 238 can be arranged to select the image data subsets by screening out those not satisfying the search criteria defined by the query, for example, those image data sets not containing the annotations "volume loss in hippocampus" or "brain tissue loss in temporal lobes".

The identified image data sets can be ranked according to the strength of matches, e.g., the number of relations in the path between the two anchors. Another ranking can be based on the number of found relations, in particular the number of different types of relations, such as relations in the anatomical and medical types described above (for "temporal lobe—brain" and "atrophy—volume loss"). For example, image data sets that are related in at most one query term (type) are discarded from the retrieval set.

The person skilled in the art will appreciate that the system can search a desired image data subset comprised in a database according to a query comprising only anatomical or diagnostic terms. For example, find a desired brain image by means of a query like "find the brain image of male patients aged 65 who have a volume difference between left and right ventricle of more than one-tenth of the left or right ventricle volume" or a query like "find the brain image of male patients aged 65 who have abnormal enlargement with hemorrhage likelihood". In such situations the selecting unit 238 is not always necessary for determining a wanted image data subset.

The person skilled in the art will also appreciate that the selecting unit 238 can be arranged to find some of the provided information in a standard way, e.g. find "the brain images of male patients aged 65" by searching the image database using conventional methods. It is most likely that this selection is done before semantic matches. Furthermore, the selecting unit may be arranged to compare the value indicated by the relevant annotations in the image reports with predefined criteria defined in the query for further screening out the image reports not satisfying the requirements of the query.

The person skilled in the art will also appreciate that the first and second medical ontology used in the above embodiments serves only to explain the different aspects of medical image cases and can be integrated as a collection of medical ontologies, for example, comprising but not limited to the UMLS and FMA.

The person skilled in the art will also appreciate that in particular situations a subset of an image data set could be the image data set itself or a collection of multiple image data subsets comprised in the image data set.

Figure 4:
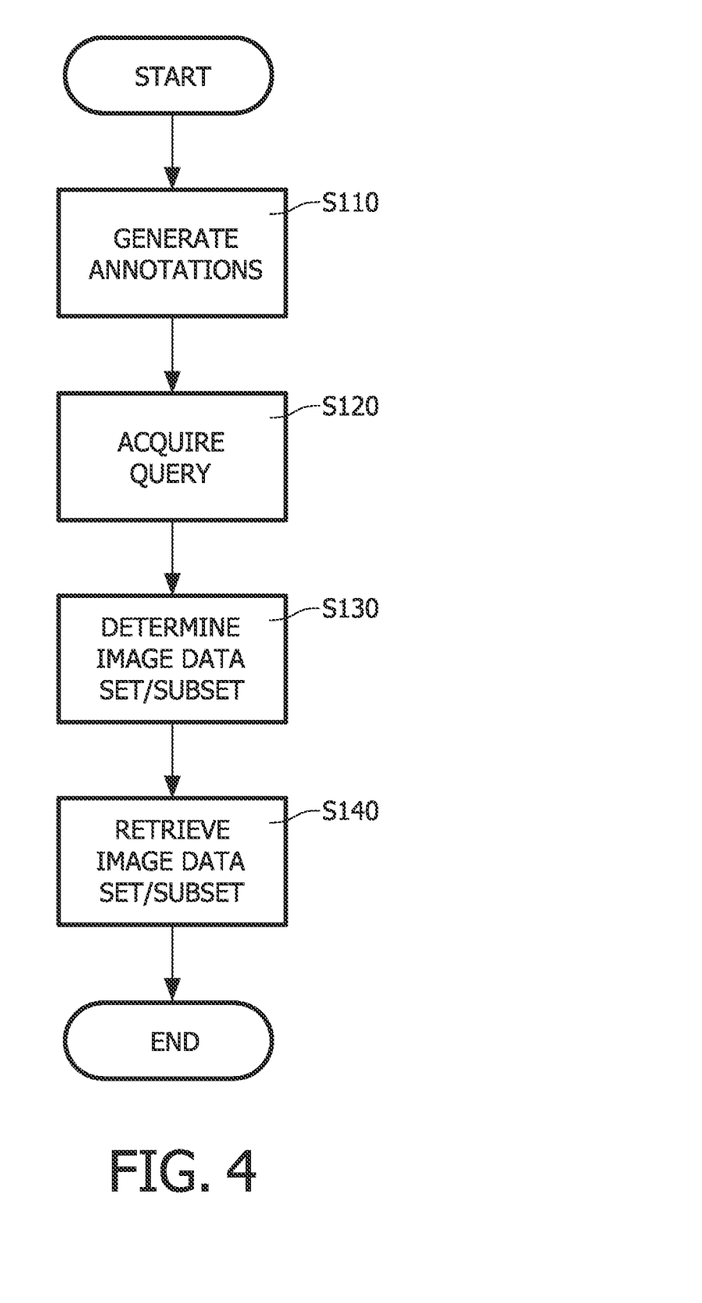
FIG. 4 is a flowchart showing an exemplary embodiment of a method in accordance with the invention.

FIG. 4 is a flowchart showing an exemplary embodiment of a method in accordance with the invention. The method of retrieving an image data set or an image data subset comprised in an image data set in a database comprising a plurality of image data sets comprises the following steps: generating medical annotations to describe image data sets in the database (S110); acquiring a query for searching the database for an image data set or an image data subset comprised in the image data set, the query comprising at least one medically relevant term defining the search criteria (S120); determining the image data set or image data subset, based on the strength of semantic matches between the at least one medically relevant term comprised in the query and (a) corresponding medical annotation(s) describing the image data set (S130); and retrieving the determined image data set or image data subset from the database (S140).The medically relevant term comprises any one of anatomically and diagnostically relevant terms, and the medical annotation comprises any one of anatomical and diagnostic annotations.

In the step S110 of the process, an image data set is segmented into a plurality of image data subsets by adapting annotated shape models, using model-based segmentation. Each of the plurality of image data subsets inherits an anatomical identifier, and associated annotations describing the image data set are transferred from corresponding annotated shape models for adaptation. The transferred anatomical identifiers and associated annotations form the original part of an original part of an electronic file describing the anatomical features of the image data set.

The electronic file can be further enriched in many ways, using additional knowledge associated with the anatomical identifier of image data subsets. For example, a new anatomical annotation can be generated and added to the electronic file, based on measures of anatomical structures, for instance the volumes or other measures of tissue, organs and lesions, in the regions identified by corresponding anatomical identifiers and computation of two measures thereof.

Furthermore, a diagnostic annotation can also be generated and added to the electronic file, based on comparison of an anatomical annotation or a computing result of two anatomical annotations and predefined criteria for use in a medical diagnosis. For example, once the anatomical regions of the brain surface and the ventricle are identified by brain ID and Ventricle ID, it is possible to calculate the ventricle-brain ratio, which can be added to the electronic file as a new anatomical annotation. Furthermore, the calculated ventricle-brain ratio can be compared with a predefined ratio defined by a radiologist or an encyclopedia for medical diagnosis of diseases like schizophrenia. The comparison result can be added to the electronic file as a diagnostic annotation that can be used in a medical diagnosis.

In step S120, a query is acquired for searching the database for a desired image data set or an image data subset described by medical annotations, which can be anatomical and/or diagnostic annotations. The query comprises at least one medically relevant term, which can be (an) anatomically and/or diagnostically relevant term(s) that define(s) the criteria for identifying the wanted image data subsets.

In step S130, an image data set or an image data subset is determined based on the strength of semantic matches between the anatomically and/or diagnostically relevant term comprised in the query and corresponding anatomical and/or diagnostic annotations describing the image data sets in the database.

In the process of determination, the anatomically and diagnostically relevant terms defined in the query are first extracted and anchored into a medical ontology. Similarly, the anatomical and diagnostic annotations describing the image data set for determination are extracted and anchored into the medical ontology.

Then the strength of semantic matches between the anatomical term comprised in the query and the anatomical annotations describing the image data set is examined based on the medical ontology to identify the image data set being described by an anatomical annotation that is semantically related to the anatomical term comprised in the query.

Similarly, the strength of semantic matches between the diagnostic term comprised in the query and the diagnostic annotations describing the image data set for determination is examined based on the medical ontology to identify the image data set being described by a diagnostic annotation that is semantically related to the diagnostic term extracted from the query.

As explained before, an anatomical or diagnostic annotation is directly or indirectly associated with at least one anatomical identifier defining an image data subset; once the image data set is identified by the semantic matches, it is not difficult to determine the desired image data subset comprised in the image data set described by the annotation(s) semantically related to the medically relevant term(s) defined in the query. For a query comprising both anatomically and diagnostically relevant term, screening is used to filter out the image data subsets not satisfying the requirements of the query.

The person skilled in the art will appreciate that some of the provided information in the query could be searched in a standard way using a conventional method that helps screen out an unwanted image data set.

In step S140, the determined image data set or image data subset is retrieved from the database. The retrieved image data subset may be directed to an output, for example, a screen to be displayed.

Figure 5:
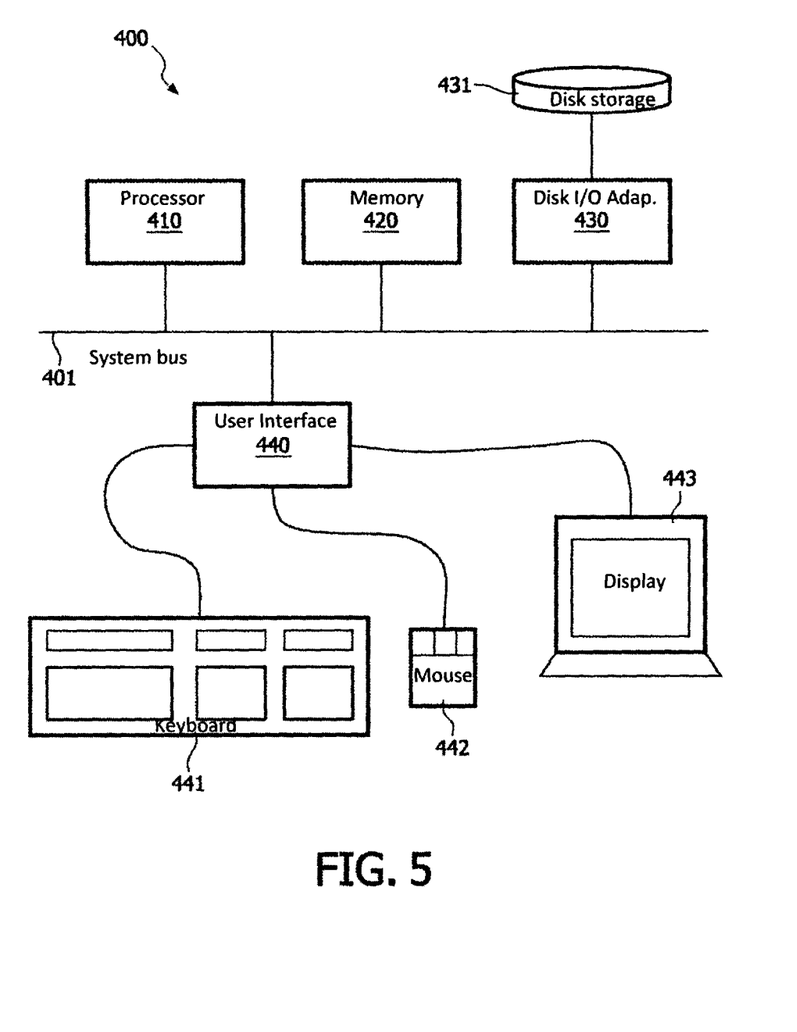
FIG. 5 schematically shows an exemplary embodiment of the workstation including the system in accordance with the invention.

FIG. 5 schematically shows an exemplary embodiment of the workstation 400. The workstation comprises a system bus 401. A processor 410, a memory 420, a disk input/output (I/O) adapter 430, and a user interface (UI) 440 are operatively connected to the system bus 401. A disk storage device 431 is operatively coupled to the disk I/O adapter 430. A keyboard 441, a mouse 442, and a display 443 are operatively coupled to the UI 440. The search system 200 of the invention, implemented as a computer program, is stored in the disk storage device 431. The workstation 400 is arranged to load the program and input data into memory 420 and execute the program on the processor 410. The user can input information, for example edit a query and input the query to the workstation 400, using the keyboard 441 and/or the mouse 442. The workstation is arranged to output information to the display device 443 and/or to the disk 431. The skilled person will understand that there are numerous other embodiments of the workstation 400 known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same item of hardware or software. The usage of the words first, second and third, et cetera, does not indicate any ordering. These words are to be interpreted as names.

The invention claimed is:

1. A system for accessing an image set database, the system comprising:
   one or more processors configured to:
      receive a query including at least one medical term based on a medical ontology and defining a search criteria;
      segment an image data set into a plurality of image data subsets based on an adapted mesh shape model, wherein at least one medical annotation annotates at least one of the segmented image data subsets, and the at least one medical annotation includes at least one of an anatomical annotation and a diagnostic annotation, and wherein the adapted mesh shape model includes the at least one medical annotation located within the mesh and an anatomical structure defined by the mesh;
      determine a strength of semantic matches between the at least one medical term and the at least one medical annotation generated by the segmentation;
      determine an image data set based on the determined strength;
      find a plurality of different types of relations between the at least one medical term and the at least one medical annotation;
      define a number, the number being the number of found different types of relations in the plurality of different types of relations;
      rank the determined image data set based on the defined number;
      retrieve a retrieval set based on the ranking;
      generate the anatomical annotation for the image data set based on a volume of at least one anatomical structure in a region identified by the adapted mesh shape model;
      extract the at least one medical term from the query;
      anchor the extracted at least one medical term into medical ontology;
      extract medical annotations describing an image data set for determination;
      anchor the extracted medical annotations into the medical ontology; and
      examine the strength of semantic matches between the anchored medical term and the anchored medical annotation based on the number of relations in a path between the two anchors;
   wherein the one or more processors are configured to generate the annotations by being configured to:
      generate a first annotation that segments a first anatomical structure in the diagnostic medical images;
      generate a second annotation that segments a second anatomical structure in the diagnostic medical images; and
      automatically generate a third annotation, the third annotation comprising a ratio between the first annotation and the second annotation;
   wherein the anchored medical term includes semantically related diagnostic terms and anatomical terms, and the anchored medical annotation includes semantically related diagnostic annotations and anatomical annotations; and
   wherein the medical ontology comprises the Foundational Model of Anatomy system and the Unified Medical Language System.

2. The system as claimed in claim 1, wherein the one or more processors are further configured to:
   generate a diagnostic annotation for the determined image data set based on:
      a comparison of an anatomical annotation with a predefined criteria for use in a medical diagnosis; and
      a comparison of two anatomical annotations of the determined image data set.

3. The system as claimed in claim 1, wherein the at least one medical term includes at least one of an anatomical term and a diagnostic term; and
   wherein the at least one medical annotation includes at least one of an anatomical annotation and a diagnostic annotation;
   wherein the one or more processors are further configured to:
      extract the at least one medical term from the query;
      anchor the extracted at least one medical term into the medical ontology;
      extract the medical annotations describing an image data set for determination;
      anchor the extracted medical annotations into the medical ontology; and
      examine the strength of semantic matches between the anchored medical term and the anchored medical annotation based on the number of relations in a path between the two anchors;
   wherein the anchored medical term includes semantically related diagnostic terms and anatomical terms, and the anchored medical annotation includes semantically related diagnostic annotations and anatomical annotations.

4. The system as claimed in claim 1, wherein image data sets that are related in at most one query term are discarded from the retrieval set.

5. A method of accessing an image set database, the method comprising:
   receiving a query comprising a medical term based on a medical ontology and defining a search criteria;
   determining a strength of semantic matches between the medical term and a medical annotation which is generated by a segmentation of the image data set into a plurality of image data subsets based on an adapted mesh shape model and the medical annotation annotates a segment of the segmented image data subsets;
   determining a path between the medical term and the medical annotation; and
   defining a number, the number being the number of relations in the path between the medical term and the medical annotation;
   wherein the strength is further determined based on the defined number;

wherein the method further comprises retrieving an image data set based on the determined strength;
wherein the medical annotation includes a diagnostic annotation, and the diagnostic annotation is generated by:
  generating a first anatomical annotation that segments a first anatomical structure in diagnostic medical images;
  generating a second anatomical annotation that segments a second anatomical structure in the diagnostic medical images;
  automatically generating a third anatomical annotation, the third anatomical annotation comprising a ratio between the first annotation and the second annotation; and
  comparing the ratio between the first anatomical annotation and the second anatomical annotation to a predefined ratio to generate the diagnostic annotation;
  wherein an additional anatomical annotation is generated for the image data set based on at least one measure of at least one anatomical structure in a region identified by the adapted mesh shape model;
wherein the at least one measure includes a volume calculation; and
wherein the medical ontology comprises the Foundational Model of Anatomy system and the Unified Medical Language System.

6. The method as claimed in claim 5, wherein the medical term comprises an anatomical term and a diagnostic term.

7. An electronic data processing device including at least one processor configured to perform the method according to claim 5.

8. A system for accessing an image set database, the system comprising:
  one or more processors configured to:
    receive a query including at least one medical term based on a medical ontology and defining a search criteria;
    segment an image data set into a plurality of image data subsets based on an adapted mesh shape model, wherein at least one medical annotation annotates at least one of the segmented image data subsets, and the at least one medical annotation includes at least one of an anatomical annotation and a diagnostic annotation, and wherein the adapted mesh shape model includes the at least one medical annotation located within the mesh and an anatomical structure defined by the mesh;
    determine a strength of semantic matches between the at least one medical term and the at least one medical annotation generated by the segmentation;
    determine an image data set based on the determined strength;
    find a plurality of different types of relations between the at least one medical term and the at least one medical annotation;
    define a number, the number being the number of found different types of relations in the plurality of different types of relations;
    rank the determined image data set based on the defined number;
    retrieve a retrieval set based on the ranking;
    generate the anatomical annotation for the image data set based on a volume of at least one anatomical structure in a region identified by the adapted mesh shape model;
    extract the at least one medical term from the query;
    anchor the extracted at least one medical term into the medical ontology;
    extract the medical annotations describing an image data set for determination;
    anchor the extracted medical annotations into the medical ontology; and
    examine the strength of semantic matches between the anchored medical term and the anchored medical annotation based on the number of relations in a path between the two anchors;
  wherein the one or more processors are configured to generate the annotations by being configured to:
    generate a first annotation that segments a first anatomical structure in the diagnostic medical images;
    generate a second annotation that segments a second anatomical structure in the diagnostic medical images; and
    automatically generate a third annotation, the third annotation comprising a ratio between the first annotation and the second annotation;
  wherein the anchored medical term includes semantically related diagnostic terms and anatomical terms, and the anchored medical annotation includes semantically related diagnostic annotations and anatomical annotations.

* * * * *